United States Patent [19]

Bellegarde

[11] 4,363,766

[45] Dec. 14, 1982

[54] PROCESS FOR THE PREPARATION OF SULFUR-CONTAINING N-BENZYL-AMINO ACIDS AND ESTERS

[75] Inventor: Bernard Bellegarde, Gradignan, France

[73] Assignee: Boehringer Ingelheim GmbH, Ingelheim, Fed. Rep. of Germany

[21] Appl. No.: 30,851

[22] Filed: Apr. 17, 1979

[30] Foreign Application Priority Data

Apr. 20, 1978 [FR] France ............................... 78 11735

[51] Int. Cl.³ .................. C07C 149/43; C07C 153/09
[52] U.S. Cl. ............................ 260/455 R; 204/59 R; 204/75; 260/544 N; 424/301; 424/309; 424/319; 560/16; 562/401; 562/426; 564/142; 564/218; 564/223; 564/305; 564/394; 564/414; 564/442; 564/443
[58] Field of Search .................. 560/16; 562/426, 401; 260/566 F, 578, 501.12, 455 R, 544 N; 204/75, 59 R; 564/305, 394, 414, 142, 218, 223, 442, 443

[56] References Cited

U.S. PATENT DOCUMENTS

4,185,114  1/1980  Baille-Barnelle et al. .......... 424/301

OTHER PUBLICATIONS

Mann et al., Chem. Abstracts, 49:15992d (1955).
El-Enany et al., Chem. Abstracts, 87:167825f (1977).

*Primary Examiner*—Vivian Garner
*Attorney, Agent, or Firm*—Hammond & Littell, Weissenberger & Muserlian

[57] ABSTRACT

A process for the preparation of sulfur-containing N-benzyl-amino acids of the formula

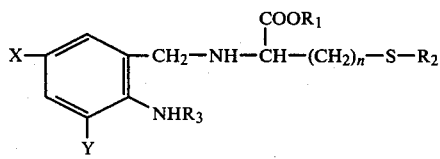

wherein
X and Y, which may be identical to or different from each other, are each hydrogen or halogen;
$R_1$ is hydrogen or alkyl of 1 to 4 carbon atoms;
$R_2$ is hydrogen, alkyl of 1 to 3 carbon atoms, carboxy-lower alkyl or acyl;
$R_3$ is hydrogen or acyl; and
n is 1 or 2;

which comprises the steps of converting anthranilic acid or a halogenated anthranilic acid into the corresponding aldehyde, reacting the aldehyde with a compound of the formula

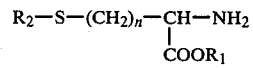

wherein $R_1$, $R_2$ and n have the meanings previously defined, to form the corresponding Schiff's base, reducing the said Schiff's base, and recovering the reaction product.

9 Claims, No Drawings

PROCESS FOR THE PREPARATION OF SULFUR-CONTAINING N-BENZYL-AMINO ACIDS AND ESTERS

This invention relates to a novel process for the preparation of sulfur-containing N-benzyl-amino acids starting from optionally halogenated anthranilic acid, as well as to optically active forms of the N-benzyl-amino acids.

More particularly, the present invention relates to a novel process for the preparation of compounds of the formula

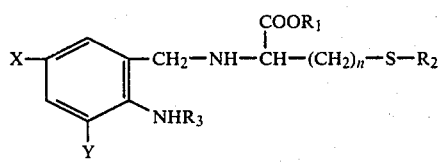

wherein
X and Y, which may be identical to or different from each other, are each hydrogen or halogen;
$R_1$ is hydrogen or straight or branched alkyl of 1 to 4 carbon atoms;
$R_2$ is hydrogen, straight or branched alkyl of 1 to 3 carbon atoms, carboxy-lower alkyl or acyl, preferably lower aliphatic acyl;
$R_3$ is hydrogen or acyl, preferably lower aliphatic acyl; and
n is 1 to 2.

THE PRIOR ART

Processes for the preparation of compounds of the formula I above and the useful pharmacological properties of the racemic forms of these compounds are disclosed in French Pat. No. 2,357,539 and copending U.S. application Ser. No. 810,087, filed June 27, 1977, now U.S. Pat. No. 4,185,114.

On a laboratory scale these processes produce satisfactory results, but on a large industrial scale, the compounds are more difficult to prepare by means of these processes, especially when X and/or Y in formula I are halogen.

For instance, pursuant to one of the prior art processes N-(2-amino-3,5-dibromo-benzyl)-methionine of the formula

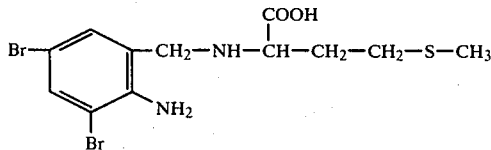

is prepared by forming a Schiff's base starting from o-nitrobenzaldehyde and methionine, hydrogenating the Schiff's base with sodium borohydride, reducing the nitro group into the amino group, and finally brominating the reaction product.

When this process is used on an industrial scale, it has several disadvantages, especially the following: The relatively high cost of the nitrobenzaldehyde; the necessity of performing the reduction of the nitro group into the amino group in hydrogen under pressure; and, moreover, the necessity of having to separate the desired end product by means of a column, because the bromination leads to the formation of unwanted side products which must be removed.

OBJECTS OF THE INVENTION

It is an object of the present invention to provide a process which makes it possible to prepare the compounds of the formula I starting from a commercial product which is readily available at relatively low cost and involves a reaction sequence that is easy to perform on an industrial scale.

Other objects and advantages of this invention will become apparent as the description thereof proceeds.

DESCRIPTION OF THE INVENTION

I have discovered that the above-stated object is achieved by a process which starts from anthranilic acid and comprises the following sequence of reaction steps:

(A) If X and/or Y in formula I are to be halogen, halogenating the anthranilic acid;

(B) Converting the optionally halogenated anthranilic acid into the corresponding aldehyde;

(C) Reacting the aldehyde with an amino acid of the formula

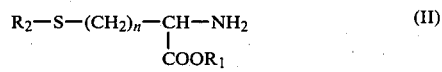

wherein $R_1$, $R_2$ and n have the same meanings as in formula I, to form the corresponding Schiff's base; and (D) Reducing the Schiff's base.

If an optically active compound of the formula II is used as the reactant in step (C), the process produces the corresponding optically active end product of the formula I, such as the levorotatory optical isomer, with high yields and purity. Such optically active isomers possess even more effective mucolytic properties than the racemic compounds of the formula I.

The conversion of the optionally halogenated anthranilic acid, i.e. reaction step (B), may be carried out in two different ways, as follows:

The first method ($a_1$) The optionally halogenated anthranilic acid is reacted with thionyl chloride to form the analogous anthranilic acid chloride;

($b_1$) The acid chloride is reacted with a secondary amine, preferably with N-methyl-aniline, to form the corresponding tertiary amide; and ($c_1$) The tertiary amide is reduced in conventional manner, for instance with lithium aluminum hydride, to yield the desired aldehyde.

The preparation of the acid chloride, i.e. step ($a_1$), is carried out in a suitable inert solvent, such as benzene or chloroform; and the preparation of the tertiary amide is performed in the presence of a basic acid-binding agent, such as triethylamine.

The second method ($a_2$) The optionally halogenated anthranilic acid is reduced to form the corresponding alcohol; and ($b_2$) The alcohol is oxidized with a metal oxide, such as manganese dioxide, to form the corresponding aldehyde.

The reduction of the optionally halogenated anthranilic acid can be effected by various methods which make it possible to convert a carboxylic acid into the corresponding alcohol. Hydrogenation methods suitable for this purpose include the following: Catalytic hydrogenation with hydrogen gas under pressure in the presence of a hydrogenation catalyst, such as a metal oxide; electrolysis in a sulfuric acid solution with lead electrodes; or reduction with a metal hydride, such as lithium aluminum hydride, or with diborane ($B_2H_6$) formed in situ. The reduction with diborane is preferred.

Because of the presence of a free $NH_2$—group when this group is unsubstituted in the anthranilic acid starting compound, the oxidation of the alcohol into the aldehyde with manganese dioxide, i.e. step ($b_2$), is performed in an apolar solvent such as chloroform, dichloroethane or dichloromethane. Chloroform is preferred as the solvent.

The optional acylation of the $NH_2$—group, that is, if $R_3$ in the intermediate aldehyde is to be acyl, can be effected on the alcohol which is obtained in step ($a_2$).

The formation of the Schiff's base in reaction step (C) is carried out in a solvent such as methanol, ethanol, isopropanol or water. The preferred solvent is methanol.

The reduction of the Schiff's base in step (D) is effected in conventional manner, for instance by means of a metal hydride, such as sodium borohydride, in water at a temperature of about 50° C.

The process of the present invention is most advantageously applied to the preparation of these compounds of the formula I wherein X and/or Y are chlorine, bromine or iodine, and especially for the preparation of the following specific compounds:
N-[(2-amino)-benzyl]-methionine,
N-[(2-amino-5-bromo)-benzyl]methionine,
N-[(2-amino-3,5-dibromo)-benzyl]-methionine,
N-[(2-amino)-benzyl]-S-methyl-cysteine,
N-[(2-amino-5-bromo)-benzyl]-S-methyl-cysteine,
N-[(2-amino-3,5-dibromo)-benzyl]-S-methyl-cysteine,
N-[(2-amino)benzyl[-S-carboxymethyl-cysteine.

The following examples illustrate the present invention and will enable others skilled in the art to understand it more completely. It should be understood, however, that the invention is not limited solely to the particular examples given below.

EXAMPLE 1

Preparation of
N-(2-amino-3,5-dibromo-benzyl)-methionine by way of the first method variation of step (B)

Step (A)—Bromination 0.5 mol of anthranilic acid were dissolved in 350 gm of methanol, the solution was heated to 40° C. while stirring, and 1 mol of bromine was added slowly. The reaction mixture was then cooled and filtered, yielding 80% of theory of 3,5-dibromo-anthranilic acid.

Step (B)—Preparation of Aldehyde

Steps ($a_1$) and ($b_1$): Preparation of anilide.

A mixture of 0.2 mol of 3,5-dibromo-anthranilic acid, 0.4 mol of thionyl chloride and 200 ml of benzene was heated for two hours. Thereafter, some of the solvent was distilled off, and a solution of 0.2 mol of N-methylaniline in benzene and 0.2 mol of triethylamine were added dropwise to the residue. The precipitated triethylamine hydrochloride was filtered off, and the filtrate was evaporated, leaving 95% of theory of 3,5-dibromo-anthranilic acid N-methylanilide.

Step ($c_1$): Preparation of aldehyde.

0.024 mol of the anilide was treated with 0.016 mol of lithium aluminum hydride at room temperature in 70 ml of tetrahydrofuran. The reaction mixture was hydrolized with dilute sulfuric acid, the tetrahydrofuran was separated, and the aldehyde, which contained 20% of the corresponding alcohol, was precipitated in water. The precipitate was collected by filtration and dried, yielding 60% of theory of 2-amino-3,5-dibromo-benzaldehyde.

Steps (C) and (D)—Preparation of Schiff's base and Reduction 0.12 mol of 2-amino-3,5-dibromo-benzaldehyde, 0.12 mol of sodium carbonate and 0.12 mol of methionine were added to an aqueous 10% methanol solution, and the mixture was heated for two hours at 50° C. Thereafter, 80 ml of water were added, the methanol was removed by evaporation, and a slight excess (5.3 gm) of sodium borohydride was added. The mixture was then stirred, either overnight at room temperature or for two hours at 50° C., the aqueous phase was made acid to pH3, and the precipitate formed thereby was collected and carefully washed with water having a pH of 3. 0.10 mol (95% of theory) of N-(2-amino-3,5-dibromo-benzyl)-methionine.$H_2O$, m.p. 198° C., was obtained. Total Yield: 35% of theory, based on anthranilic acid starting material.

EXAMPLE 2

Preparation of
N-(2-amino-3,5-dibromo-benzyl)-methionine by way of the second method variation of step (B)

Step (A)—Bromination

Same as in Example 1.

Step (B)—Preparation of Adelhyde

Step ($a_2$): Preparation of alcohol

A solution of 0.04 mol of borontrifluoride etherate in 15 ml of tetrahydrofuran was slowly added to a solution of 0.03 mol of sodium borohydride and 0.01 mol of 3,5-dibromoanthranilic acid in 25 ml of tetrahydrofuran which had been cooled to 10° C., and the mixed solution was refluxed for two hours. Thereafter, the alcohol was separated by hydrolysis, and the tetrahydrofuran was evaporated (precipitation of the aqueous phase). Based on the anthranilic acid starting material, the yield of 3,5-dibromo-anthranilic alcohol was close to 100%.

Step ($b_2$): Preparation of aldehyde.

A mixture of 28 gm. (0.1 mol) of 3,5-dibromo-anthranilic alcohol, 200 ml of chloroform and 70 gm of manganese oxide was refluxed for three hours. Thereafter, the reaction mixture was filtered, and the solvent was evaporated from the filtrate, yielding 2-amino-3,5-dibromo-benzaldehyde containing not even a trace of the alcohol. The yield of aldehyde was virtually quantitative when the losses during the evaporation of the solvent were held to a minimum.

Steps (C) and (D)—Preparation of Schiff's Base and Reduction

Same as in Example 1.

Total yield of N-(2-amino-3,5-dibromo-benzyl)-methionine, based on anthranilic acid starting material: 68% of theory.

EXAMPLE 3

Preparation of N-(2-amino-benzyl)-methionine by way of anthranil alcohol

Anthranil alcohol

A solution of 0.1 mol of anthranilic acid in tetrahydrofuran was treated with 0.3 mol of diborane. After hydrolysis and precipitation, anthranil alcohol was obtained with a yield of 90% of theory.

Anthranil aldehyde

The alcohol in solution in chloroform was treated with an excess of manganese dioxide. After refluxing for three hours the reaction mixture was filtered, yielding 85% of theory of anthranil aldehyde.

N-(2-amino-benzyl)-methionine:

A mixture of 0.1 mol of anthranil aldehyde, 0.1 mol of methionine and a solution of 0.1 mol of sodium carbonate in 50 ml of water was stirred for a few hours. After everything had gone into solution, 0.1 mol of sodium borohydride was added, and the mixture was stirred at room temperature for 12 hours. The reaction solution was then acidified to pH3, and the precipitate was collected and dried, yielding 85% of theory of N-(2-amino-benzyl)-methionine, m.p. 198° C. The total yield, based on the anthranilic acid starting material, was 68% of theory.

EXAMPLE 4

Preparation of optically active L-N-(2-amino-3,5-dibromo-benzyl)-methionine 0.12 mol of 2-amino-3,5-dibromo-benzaldehyde, 0.12 mol of sodium carbonate and 0.12 mol of L-methionine were added to 100 ml of methanol, and the mixture was heated at 50° C. for two hours. Thereafter, 80 ml of water were added, the methanol was evaporated, and a slight excess (5.3 gm) of sodium borohydride was added to the residue. The mixture was stirred overnight at room temperature. Thereafter, the aqueous phase was acidified to pH3, and the precipitate formed thereby was collected and carefully washed with water having a pH of 3. 0.9 mol (75% of theory) of L-N-(2-amino-3,5-dibromo-benzyl)-methionine, optical rotation—237.4° (c=1% in 0.1 N NaOH), m.p. 204° C., was obtained.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. A process for the preparation of a compound of the formula

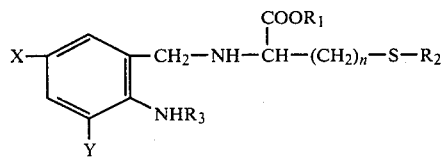

wherein
X and Y, which may be identical to or different from each other, are each hydrogen or halogen;
$R_1$ is hydrogen or alkyl of 1 to 4 carbon atoms;
$R_2$ is hydrogen, alkyl of 1 to 3 carbon atoms, carboxy-lower alkyl or lower aliphatic acyl;
$R_3$ is hydrogen or lower aliphatic acyl; and
n is 1 or 2;
which comprises the steps of
(A) converting anthranilic acid or a halogenated anthranilic acid into the corresponding aldehyde by
 (a) reacting the optionally halogenated anthranilic acid with thionyl chloride to form the corresponding anthranilic acid chloride, reacting the acid chloride with a secondary amine to form the corresponding tertiary amide, and reducing the tertiary amide; or
 (b) reducing the optionally halogenated anthranilic acid to form the corresponding alcohol, and oxidizing the said alcohol with a metal oxide;
(B) reacting the aldehyde with a racemic or optically active compound of the formula

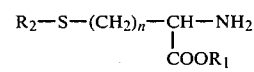

wherein $R_1$, $R_2$ and n have the meanings previously defined, to form the corresponding Schiff's base;
(C) reducing the said Schiff's base; and
(D) recovering the reaction product.

2. A process of claim 1, wherein the conversion of the anthranilic acid or halogenated anthranilic acid into the corresponding aldehyde is effected by reacting the optionally halogenated anthranilic acid with thionyl chloride to form the corresponding anthranilic acid chloride, reacting the acid chloride with a secondary amine to form the corresponding tertiary amide, and reducing the tertiary amide.

3. A process of claim 2, wherein said secondary amine is N-methyl-aniline and said tertiary amide is reduced with lithium aluminum hydride.

4. A process of claim 1, wherein the conversion of the anthranilic acid or halogenated anthranilic acid into the corresponding aldehyde is effected by reducing the optionally halogenated anthranilic acid to form the corresponding alcohol, and oxidizing the said alcohol with a metal oxide.

5. A process of claim 4, wherein the reduction of the optionally halogenated anthranilic acid is effected by catalytic hydrogenation with hydrogen in the presence of a metal oxide hydrogenation catalyst, and the alcohol is oxidized with manganese dioxide.

6. A process of claim 4, wherein the reduction of the optionally halogenated anthranilic acid is effected by electrolysis in sulfuric acid with lead electrodes.

7. A process of claim 4, wherein the reduction of the optionally halogenated anthranilic acid is effected by means of a metal hydride.

8. A process of claim 7, wherein said metal hydride is lithium aluminum hydride or diborane produced in situ.

9. A process of claim 7, wherein said metal hydride is diborane produced in situ.

* * * * *